United States Patent [19]

Takahashi et al.

[11] Patent Number: 5,752,912
[45] Date of Patent: May 19, 1998

[54] MANIPULATOR FOR FLEXIBLE PORTION OF AN ENDOSCOPE

[75] Inventors: Hisaki Takahashi; Shizuharu Miura; Kikuo Iwasaka, all of Tokyo, Japan

[73] Assignee: Asahi Kogaku Kogyo Kabushiki Kaisha, Tokyo, Japan

[21] Appl. No.: 666,041

[22] Filed: Jun. 19, 1996

[30] Foreign Application Priority Data

Jun. 26, 1995 [JP] Japan .................................. 7-159023
Jul. 4, 1995 [JP] Japan .................................. 7-168437

[51] Int. Cl.[6] .................................. A61B 1/00
[52] U.S. Cl. .................... 600/149; 600/146; 600/148; 600/150
[58] Field of Search .................... 600/139, 146–150

[56] References Cited

U.S. PATENT DOCUMENTS

| | | | |
|---|---|---|---|
| 3,162,214 | 12/1964 | Bazinet | 600/146 X |
| 3,892,228 | 7/1975 | Mitsui | 600/149 |
| 4,294,233 | 10/1981 | Takahashi | 600/149 |
| 4,483,326 | 11/1984 | Yamaka et al. | 600/149 |
| 4,928,669 | 5/1990 | Sullivan | 600/144 |
| 4,960,106 | 10/1990 | Kubokawa et al. | 600/104 |
| 5,058,568 | 10/1991 | Irion et al. | 600/146 X |
| 5,158,086 | 10/1992 | Brown et al. | 128/662.03 |
| 5,170,775 | 12/1992 | Tagami | 356/241 |
| 5,549,542 | 8/1996 | Kovalcheck | 600/146 |

*Primary Examiner*—Beverly M. Flanagan
*Attorney, Agent, or Firm*—Kane,Dalsimer,Sullivan, Kurucz, Levy, Eisele and Richard, LLP

[57] ABSTRACT

A manipulator for a flexible portion of an endoscope includes a rotatable pulley provided in an operating portion of the endoscope, and a pliable pull rope which is wound about the pulley. One end of the pull rope is connected to the pulley. The flexible front end portion is provided at an insertion portion of the endoscope to be remotely bendable through the pull rope when the pull rope is pulled in accordance with a rotation of the pulley. The pull rope is made of braided non-metallic fibers so as to have a high pliability.

6 Claims, 3 Drawing Sheets

MANIPULATOR FOR FLEXIBLE PORTION OF AN ENDOSCOPE

BACKGROUND OF THE INVENTION

1. Field of the Invention

The present invention relates to an endoscope having a flexible front end portion provided at the front end of an insertion portion, and particularly relates to a manipulator using an operation wire which is pulled in accordance with a rotation of a pulley to manipulate the flexible portion of the endoscope.

2. Description of the Related Art

An endoscope having a manipulator for a flexible portion, provided at a front end of an insertion portion of the endoscope, is widely known, in which operation wires are pulled remotely by an operating portion to bend the flexible portion.

In such a type of endoscope, the operating portion is provided therein with a pulley which is rotated by a knob, about which pull wires (usually two pull wires) are wound to pull the operation wires. Each of the pull wires is made of stranded fine stainless steel wires. Namely, the pull wires are each made of, for example, 7 wire strands, each wire strand being made of 7 stranded wire threads each having a diameter of 0.1 mm, i.e., each pull wire is made of 7 stranded wire threads having 7 wire strands. Consequently, each of the pull wires has an outer diameter of 0.9 mm, and a certain amount of pliability. However, the amount of pliability of the pull wires, made of stainless steel, is insufficient so that a strong force is necessary to wind the pull wires around the pulley.

The pull wires are respectively connected at one end thereof to the pulley and at the other end to the respective operation wires. Slack absorbing devices are provided at connections between the pull wires and the operation wires to absorb the slack of the operation wires.

When one of the pull wires is pulled, a difference in the expansion of the wires (strands) of which the pull wire is made, is caused between the inner peripheral portion and the outer peripheral portion thereof due to a difference in tension exerted thereon. Consequently, no load can be uniformly distributed in the pull wire. Furthermore, through repeated pull operations of the pull wires with respect to the pulley, metal fatigue is caused, resulting in damage to the pull wires. Consequently, the wires (strands) of the pull wires are partly frayed, and eventually the pull wires are completely frayed or broken.

Before the pull wires are completely frayed, the outer portions thereof that are located around the frayed wire threads are worn or damaged by rubbing against the latter.

Moreover, the miniaturization of the pulley to reduce the operation torque of the operation knob is limited due to the insufficient amount of pliability of the pull wires.

SUMMARY OF THE INVENTION

It is an object of the present invention to provide a manipulator for a flexible portion of an endoscope in which the pull wires wound around the pulley can not be easily frayed or broken, thus leading to an increased durability, and the operation torque of the operation knob can be reduced.

To achieve the object mentioned above, according to an aspect of the present invention, a manipulator for a flexible front end portion of an endoscope is provided having a rotatable pulley provided in an operating portion of the endoscope, and a pliable pull rope which is wound about the pulley. One end of the pull rope is connected to the pulley. The flexible front end portion is provided at an insertion portion of the endoscope to be remotely bendable through the pull rope, when the pull rope is pulled in accordance with a rotation of the pulley. The pull rope is made of braided non-metallic fibers so as to have a high pliability.

Preferably, an operation wire is connected to another end of the pull rope and is also connected to the flexible front end portion.

It is preferred that at least a portion of the pull rope wound around the pulley is provided with a synthetic resin layer coated thereon, or with a tubular protection mesh layer made of fine metal wires.

According to another aspect of the present invention, an endoscope having an insertion portion, a flexible front end portion provided at a front end of the insertion portion and an operating portion connected to a rear end of the insertion portion is provided, having a rotatable pulley provided in the operating portion, and a pliable pull rope which is wound about the pulley. The rotatable pulley being manually operable to rotate clockwise and counterclockwise. One end of the pull rope is connected to the pulley, while another end of the pull rope extends outwardly from the pulley. An operation wire is also provided, one end of which is connected to the end of the pull rope which extends outwardly from the pulley, and another end of the operation wire is connected to the flexible front end portion to remotely operate the flexible front end portion through the pull rope, when the pull rope is pulled in accordance with a rotation of the pulley. The pull rope is made of braided non-metallic fibers so as to have a high pliability.

Preferably, at least a portion of the pull rope wound around the pulley is provided with a synthetic resin layer coated thereon, or with a tubular protection mesh layer made of fine metal wires.

The present disclosure relates to subject matter contained in Japanese Patent Application No.7-159023 (filed on Jun. 26, 1995) and Japanese Patent Application No.7-168437 (filed on Jul. 4, 1995) which are expressly incorporated herein by reference in their entirety.

BRIEF DESCRIPTION OF THE DRAWINGS

The present invention will be discussed below in detail with reference to the accompanying drawings, in which like members are indicated by like reference numerals, and wherein.

DESCRIPTION OF THE PREFERRED EMBODIMENT

Figure 5:
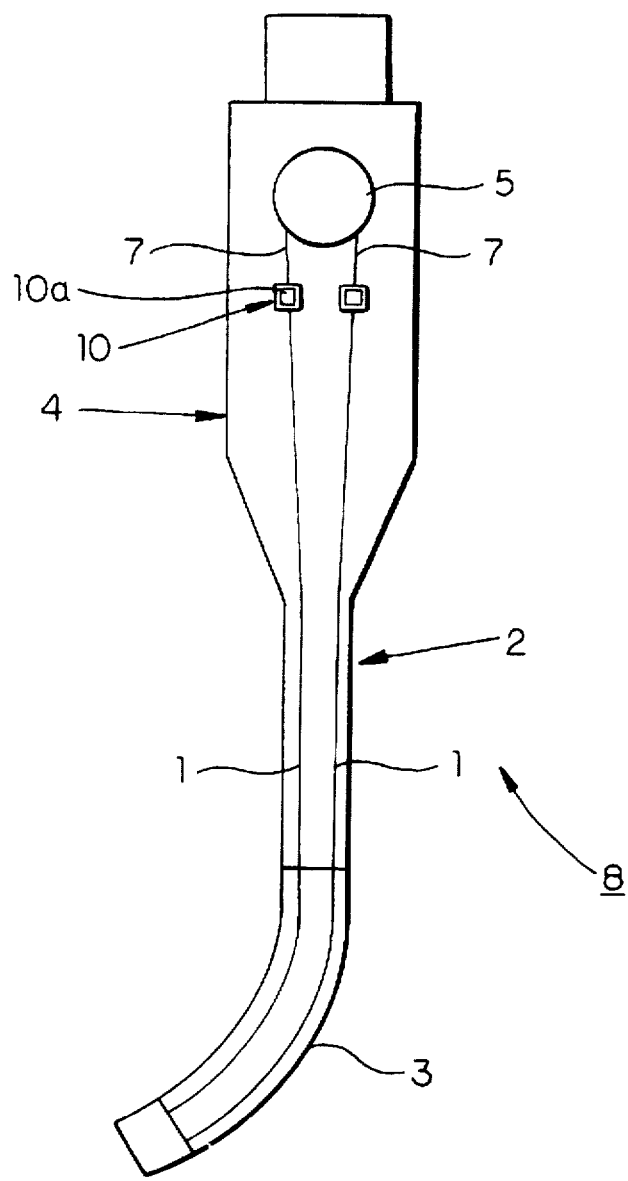
FIG. 5 is a schematic view of an endoscope to which the present invention is applied.

FIG. 5 shows an endoscope 8 to which the present invention is applied. An insertion portion 2 of the endoscope 8 is provided on a front end thereof with a flexible portion 3 which can be bent by a remote operation, and on a base end thereof with an operating portion 4.

Operation wires 1, used to move the flexible portion 3, are connected at front ends thereof to the front end of the flexible portion 3 and extend at the base ends thereof into the operating portion 4. The operation wires 1 are guided by respective guide tubes (not shown) provided within the insertion portion 2.

The operating portion 4 is provided therein with a pulley 5 which is rotated by -an operation knob (not shown). Two pull ropes 7 are wound around the pulley 5 to pull the operation wires 1.

Each of the pull ropes 7 is made of braided non-metallic fibers to exhibit a high pliability. For example, four bundles of threads are braided. The number of bundles of threads is not limited to four, and can be, for example, 8 or 16.

One end of each of the pull ropes 7 is secured to the pulley 5 and the other end of the pull ropes 7 is connected to the operation wires 1 through connectors 10. The pliable pull ropes 7 of the present invention can be locally bent at any portion thereof. Slack of each of the operation wires 1 can be absorbed due to the pliability of the associated pull rope 7. Consequently, the connectors 10 can be adapted to only connect the pull ropes 7 and the operation wires 1, namely, it is not necessary for the connectors 10 to have a slack absorbing function.

Figure 1:
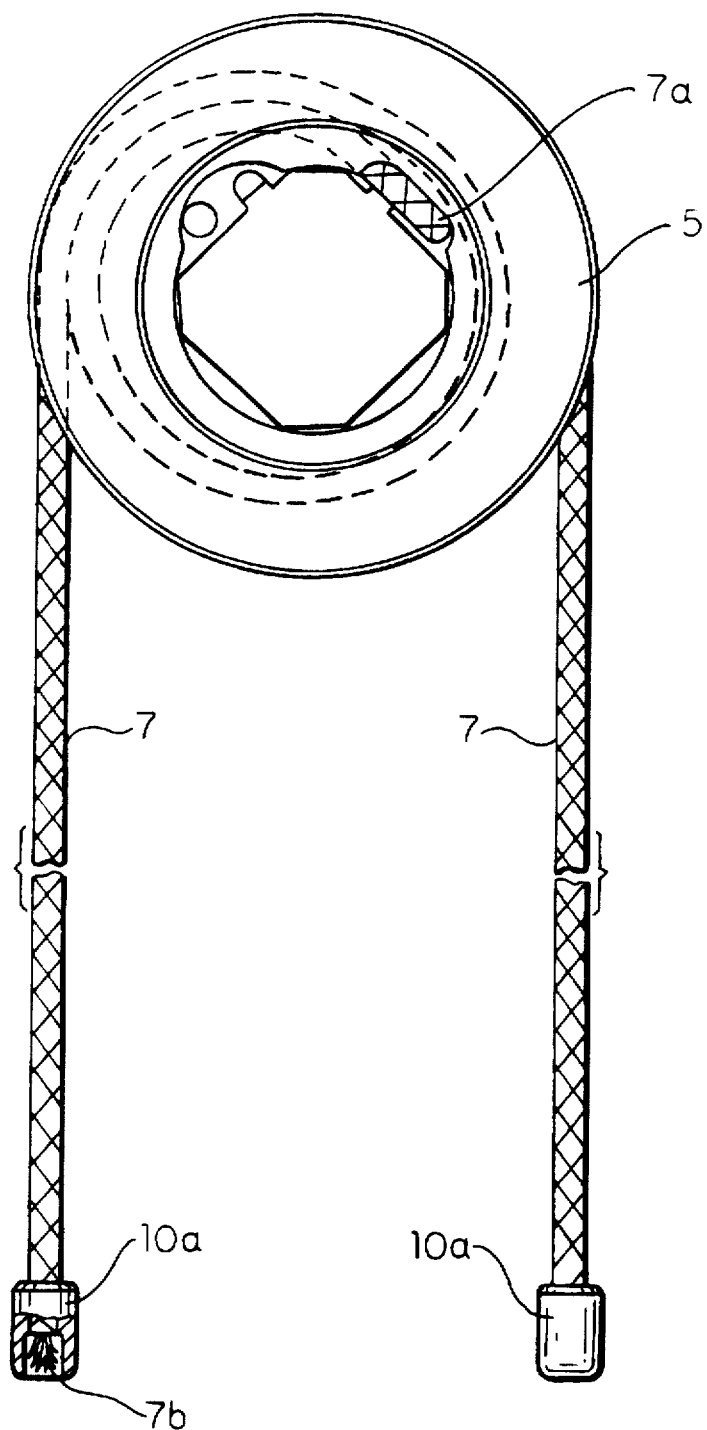
FIG. 1 is a front elevational view of a pulley and pull ropes of a manipulator of an endoscope according to the present invention.

FIG. 1 shows an enlarged view of the pulley 5 and the pull ropes 7. In FIG. 1, the base end of the right (as viewed in FIG. 1) pull rope 7 to be connected to the pulley 5 is located behind the pulley 5 and accordingly is not shown. The connectors 10 connected to outer ends 7b of the pull ropes 7 include collars 10a which are provided with stepped holes 10b (FIG. 2) through which the pull ropes 7 extend. The stepped holes 10b are provided with large diameter portions 10c at the ends thereof adjacent to the operation wires 1.

Figure 2:
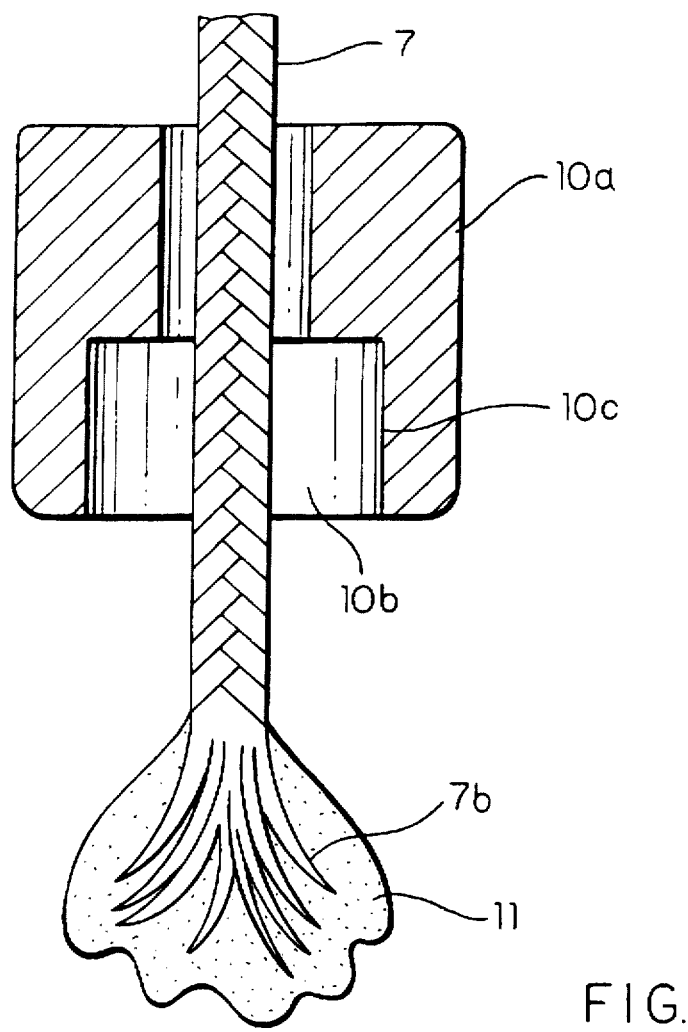
FIG. 2 is an enlarged sectional view of an outer end of a pull rope and a collar secured thereto in the manipulator according to the present invention.

To secure the collar 10a to the pull rope 7, the pull rope 7 is inserted into the collar 10a, and then the end of the pull rope 7 is unbraided or knotted. Thereafter, the unbraided or knotted end of the pull rope 7 is bonded to the large diameter portion 10c of the stepped hole 10b of the collar 10a by an adhesive 11 or the like, as shown in FIG. 2.

Alternatively, it is possible that, after the outer end of the pull rope 7 is unbraided, the adhesive 11 is applied to the surfaces of the unbraided fibers, so that the outer end of the pull rope 7 can be secured to the large diameter portion 10c of the stepped hole 10b of the collar 10a.

Figure 3:
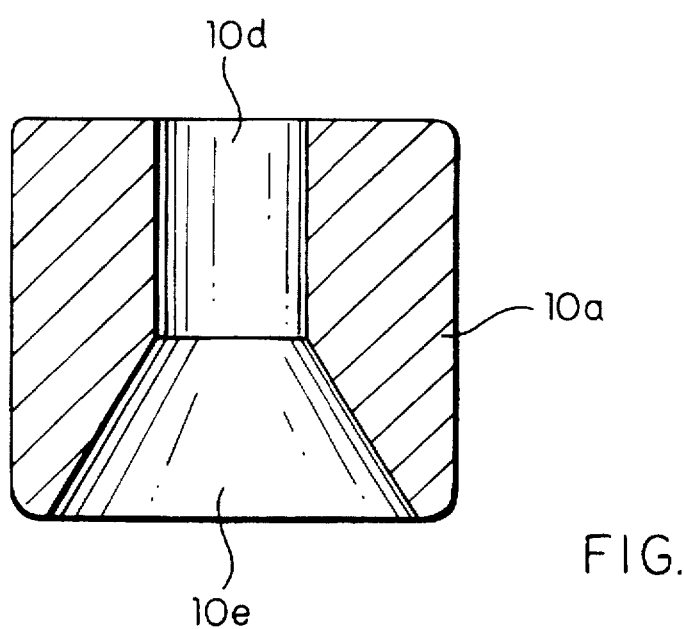
FIG. 3 is an enlarged sectional view of another collar according to the present invention.

Preferably, the surfaces of the unbraided fibers are subject to a chemical liquid treatment to enhance the affinity to the adhesive 11 prior to the connection of the pull ropes 7 to the collars 10a. FIG. 3 shows a modified collar 10a which is provided with an insertion hole 10d having a conical hole portion 10e.

While the above discussion is directed to the outer ends 7b of the pull ropes 7, it can also be equally applied to the other ends (inner ends) 7a of the pull ropes 7. Namely, the inner ends 7a of the pull ropes 7 can be secured to the pulley 5 in the same way as the outer ends 7b.

Figure 4:
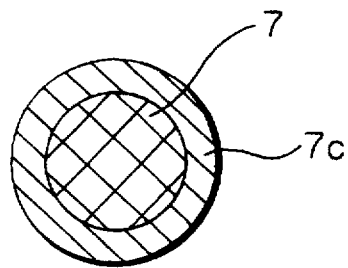
FIG. 4 is a sectional view of a pull rope with an outer sheath, according to the present invention.

It is possible to coat the pull ropes 7 with an outer cover to increase durability. For instance, the pull rope 7 shown in FIG. 4 has an outer diameter of approximately 0.7 or 0.8 mm and is coated or covered by a synthetic resin sheath (cover layer) 7c which extends throughout substantially the whole length of the pull rope 7. The thickness of the sheath 7c is 0.05 mm to 0.1 mm so as to maintain the high pliability of the pull ropes 7.

The cover layer 7c can be formed by extrusion in which the synthetic resin is extruded onto and impregnated into the outer surface of the pull rope 7 or a heat shrinking process in which a heat-shrinkable tube is applied and heated onto the outer surface of the pull rope 7.

The outer cover layer 7c can be made of PTFF (fluoroplastics) or nylon for extrusion, or fluoroplastics or polyethylene for the heat-shrinkable tube. However, the form of the outer cover layer is not limited to the foregoing, for example, it is not necessary to provide the synthetic resin layer 7c throughout the whole length of the pull rope 7. The outer cover layer 7c can be provided at least on the portion of the pull rope 7 that is wound about the pulley 5. The synthetic resin layer 7c can be replaced by a tubular layer of a meshed metal wire, such as a fine tungsten wire having an outer diameter of approximately 0.02 mm.

As can be understood from the foregoing, according to the present invention, since the pull ropes wound about the pulley to pull the operation wires are made of braided non-metallic fibers, the pull ropes are so pliable that they can be easily bent along the outer peripheral surface of the pulley when the pull ropes are pulled to bend the flexible portion of the endoscope. Moreover, unlike the case of the metal wire, repeated pull operations causes no metal fatigue of the ropes, and hence no fraying or breakage thereof tends to occur. Even if the non-metallic fibers of the pull ropes do fray, the surrounding or adjacent non-metallic fibers are not damaged thereby. Moreover, since the pull ropes are expandable and pliable to absorb the slackness of the operation wires, no slackness absorbing device is necessary.

In addition to the foregoing, since the durability (pliability) of the pull ropes for the pulley of the same diameter can be increased, a smaller diameter pulley can be employed to reduce the operation torque of the operation knob.

If the portions of the pull ropes that are wound about the pulley are covered by a synthetic resin layer or a meshed tube of metal wires, the pull ropes can be protected from being damaged by the edge of the pulley, thus resulting in an increased durability of the pull ropes.

Although the present invention has been described with reference to particular means and materials, it is to be understood that the invention is not limited to the particulars disclosed and extends to all equivalents within the scope of the claims.

What is claimed is:

1. A manipulator for a flexible front end portion of an endoscope, comprising:

a rotatable pulley provided in an operating portion of said endoscope;

a pliable pull rope which is wound about said pulley, a first end of said pull rope being connected to said pulley; and an operation wire connected to a second end of said pull rope and connected to said flexible front end portion;

wherein said flexible front end portion is provided at an insertion portion of said endoscope, said flexible front end portion being remotely bendable by said pull rope when said pull rope is pulled in accordance with a rotation of said pulley, and wherein said pull rope is made of braided non-metallic fibers so as to have a high pliability.

2. The manipulator for a flexible front end portion of an endoscope according to claim 1, wherein at least a portion of said pull rope wound around said pulley is provided with a synthetic resin layer coated thereon.

3. The manipulator for a flexible front end portion of an endoscope according to claim 1, wherein at least a portion of said pull rope wound around said pulley is provided with a tubular protection mesh layer made of fine metal wires.

4. An endoscope having an insertion portion, a flexible front end portion provided at a front end of said insertion portion and an operating portion connected to a rear end of said insertion portion, comprising:

- a rotatable pulley provided in said operating portion, said rotatable pulley being manually operable to rotate clockwise and counterclockwise;
- a pliable pull rope which is wound about said pulley, a first end of said pull rope being connected to said pulley, a second end of said pull rope extending outwardly from said pulley; and
- an operation wire, a first end of said operation wire being connected to said second end of said pull rope, and a second end of said operation wire being connected to said flexible front end portion, said flexible front end portion being remotely operable by said pull rope when said pull rope is pulled in accordance with a rotation of said pulley;

wherein said pull rope is made of braided non-metallic fibers so as to have a high pliability.

5. The endoscope having a flexible front end portion according to claim 4, wherein at least a portion of said pull rope wound around said pulley is provided with a synthetic resin layer coated thereon.

6. The endoscope having a flexible front end portion according to claim 4, wherein at least a portion of said pull rope wound around said pulley is provided with a tubular protection mesh layer made of fine metal wires.

* * * * *